(12) United States Patent
Pamparana

(10) Patent No.: US 7,462,643 B1
(45) Date of Patent: Dec. 9, 2008

(54) ESSENTIAL FATTY ACIDS IN THE PREVENTION OF CARDIOVASCULAR EVENTS

(75) Inventor: Franco Pamparana, Milan (IT)

(73) Assignee: Pfizer Italia S.R.L., Latina (IT)

( * ) Notice: Subject to any disclaimer, the term of this patent is extended or adjusted under 35 U.S.C. 154(b) by 0 days.

(21) Appl. No.: 09/869,333

(22) PCT Filed: Feb. 7, 2000

(86) PCT No.: PCT/EP00/00957

§ 371 (c)(1),
(2), (4) Date: Jul. 26, 2001

(87) PCT Pub. No.: WO00/48592

PCT Pub. Date: Aug. 24, 2000

(30) Foreign Application Priority Data

Feb. 17, 1999 (IT) .............................. MI99A0313

(51) Int. Cl.
*A61K 31/22* (2006.01)
*A61K 31/20* (2006.01)

(52) U.S. Cl. .................................. 514/549; 514/560
(58) Field of Classification Search ................ 514/549, 514/560
See application file for complete search history.

(56) References Cited

U.S. PATENT DOCUMENTS

| | | | |
|---|---|---|---|
| 4,920,098 A | 4/1990 | Cotter et al. | |
| 5,130,061 A | 7/1992 | Cornieri et al. | |
| 5,208,236 A | 5/1993 | Neustadt | |
| 5,502,077 A * | 3/1996 | Breivik et al. ............... | 514/560 |
| 5,656,667 A | 8/1997 | Breivik et al. | |
| 5,683,997 A | 11/1997 | Buhlmayer et al. | |
| 5,698,594 A | 12/1997 | Breivik et al. | |
| 5,753,703 A | 5/1998 | Cavazza et al. | |
| 5,760,081 A * | 6/1998 | Leaf et al. ................... | 514/560 |
| 6,159,993 A | 12/2000 | Seed et al. | |
| 6,313,167 B1 | 11/2001 | Nakajima et al. | |
| 6,333,447 B1 | 12/2001 | Homcy et al. | |
| 6,627,604 B2 | 9/2003 | Vertesy et al. | |

FOREIGN PATENT DOCUMENTS

| | | |
|---|---|---|
| CN | 1082909 | 3/1994 |
| EP | 0255824 | 2/1988 |
| EP | 0409903 | 1/1991 |
| EP | 0587269 A2 | 6/1993 |
| EP | 0689838 A1 | 1/1996 |
| EP | 0699437 A1 | 3/1996 |
| EP | 0292846 B1 | 11/1998 |
| GB | 2218984 | 11/1989 |
| GB | 2 221 843 | 2/1990 |
| HU | 9802308 | 2/1999 |
| IT | 1235879 | 11/1992 |
| JP | 4029928 | 1/1992 |
| JP | 7118229 | 5/1995 |
| WO | WO 8911521 | 11/1989 |
| WO | WO 9810085 | 3/1998 |
| WO | WO 0048592 | 8/2000 |

OTHER PUBLICATIONS

The Nutrition Desk Reference, Garrison, et al., published 1985 by Keats Publishing, Inc. (CT), pp. 150-151.*
Harrison's Principles of Internal Medicine, 13th Edition, vol. 1, published 1994 by McGraw-Hill, Inc., pp. 1066-1077.*
Hagstrup et al., "Effect of fish oil on heart rate variability in survivors of myocardial infarction: a double blind randomized trial", BMJ, vol. 312, Mar. 16, 1996, pp. 677-678.*
Singh et al., "Randomized, Double-Blind, Placebo-Controlled Trial of Fish Oil and Mustard Oil in Patients with Suspected Actue Myocardial Infarction: The Indian Experiment of Infarct Survival—4", Cardiovascular Drugs and Therapy 1997; 11:485-491.*
Lancet: vol. 2, Issue 8666, Sep. 30, 1989, pp. 757-761.
Lancet: vol. 343, Issue 8911, Jun. 11, 1994, pp. 1454-1459.
Japanese patent application JP04029928 (Derwent: 1992-085863), (1992).
Giornale Italiano di Cardiologia: 1993 (23), 1053-1061.
Giornale Italiano de Cardiologia: vol. 23, Oct. 1993, 1053-1061.
British National Formulary, No. 8, 1989, Chapter 2: Cardiovascular System, British Medical Association and the Royal Pharmaceutical Society of Britain.
Burr, et al., "Effects on Changes in Fat, Fish, and Fibre Intakes on Death and Myocardial Reinfarction: Diet and Reinfarction Trial (Dart)," The Lancet, 1989:757-761.
Burr, et al., "Diet and Reinfarction Trail (DART): Design, Recruitment, and Compliance," Europea Heart Journal, vol. 10, 1989:558-567.

(Continued)

Primary Examiner—Raymond J Henley, III
(74) Attorney, Agent, or Firm—Arent Fox LLP

(57) ABSTRACT

The invention concerns the use of essential fatty acids with a high content in eicosapentaenoic acid ethyl ester (EPA) or docosahexaenoic acid ethyl ester (DHA) or a high concentration mixture thereof in the preparation of a medicament useful for preventing mortality, in particular due to sudden death, in patients who have suffered from a myocardial infarction.

26 Claims, No Drawings

OTHER PUBLICATIONS

Luley, et al., "Bioavailability of Omega-3 Fatty Acids: Ethylester Preparations are as Suitable as Triglyceride Preparations," Akt. Ernähr.—Med., vol. 15, 1990:123-125.

Norday, et al., "Absorption of the n-3 Eicosapentaenoic and Docosahexaenoic Acids as Ethyl Esters and Triglycerides by Humans[1-3]," American Society for Clinical Nutrition, vol. 53, 1991:11-5-1190.

Schmidt, et al., "n-3 Fatty Acids: Prevention and Treatment in Vascular Disease," Bi & Gi Publisher, Verona—Springer Vertag, London, 1995.

Singh, et al., "Randomized, Double-Blind, Placebo-Controlled Trail of Fish Oil and Mustard Oil in Patients with Suspected Acute Myocardial Infarction: The Indian Experiment of Infarct Survival—4," Cardiovascular Drugs and Therapy, vol. 11, 1997:485-491.

GISSI-Prevenzione Investigators, "Dietary Supplementation with N-3 Polyunsaturated Fatty Acids and Vitamin E After myocardial Infarction: Results of the GISSI-Prevenzione Trial," The Lancet, vol. 354, 1999:447-455.

Marchioli, et al., The Results of the GISSI-Prevenzione trial in the General Framework of Secondary Prevention, European Heart Journal, vol. 21, 2000:949-952.

R. Marchioli, "Treatment with n-3 Polyunsaturated Fatty Acids After Myocardial Infarction: Results of GISSI-Prevenzione Trial," European Heart Journal Supplements, vol. 3, 2001:D85-D97.

Preffer, "Left Ventricular Remodeling in Acute Myocardial Infarction," *Annu. Rev. Med.* 46:455-66 (1995).

Ryan, et al., "ACC/AHA Guidelines for the Management of Patients with Acute Myocardial Infarction: A Report of the American College of Cardiology/American Heart Association Task Force on Practice Guidelines (Committee on Management of Acute Myocardial Infarction," *J Am Coll Cardiol* 28:1328-1428 (1996).

Ryan, et al., "1990 Update: ACC/AHA Guidelines for the Management of Patients with Acute Myocardial Infarction: A Report of the American College of Cardiology/American Heart Association Task Force on Practice Guidelines (Committee on Management of Acute Myocardial Infarction," *J Am Coll Cardiol* 34:890-911 (1999).

Antman, et al., "ACC/AHA Guidelines for the Management of Patients with ST-Elevation Myocardial Infarction: Executive Summary: A Report of the ACC/AHA Task Force on Practice Guidelines (Committee to Revise the 1999 Guidelines on the Management of Patients with Acute Myocardial Infarction)," Circulation 110:1-49 (2004).

Harrison, et al., "The Mechanism of Action of Omega-3 Fatty Acids in Secondary Prevention Post-Myocardial Infarction," *Curr Med Res Opin* 21(1):95-100 (2005).

GISSI-Prevenzione Investigators, *Dietary supplementation with n-3 polyunsaturated fatty acids and vitamin E after myocardial infarction: results of the GISSI-Prevenzione trial*, The Lancet (1999) vol. 354, 447-455.

Christine M. Albert, M.D., et al., *Blood Levels of Long-Chain n-3 Fatty Acids and the Risk of Sudden Death*, N. Engl J. Med, (2002) vol. 346, No. 15, 1113-1118.

Maggie B. Covington, M.D., *Omega-3 Fatty Acids*, American Family Physician (2004), vol. 74, No. 1, 133-140.

Chenchen Wang MD et al., *Effects of Omega-3 Fatty Acids on Cardiovascular Disease*, AHRQ Publication No. 04-E009-2 (2004) Evidence Report/Technology Assessment No. 94.

TRICOR® 48 mg and 145 mg, (fenofibrate tablets), Abbott Laboratories (2004) pp. 1-8.

The Field Study Investigators, *Effects of long-term fenofibrate therapy on cardiovascular events in 9795 people with type 2 diabetes mellitus (the FIELD study): randomized controlled trial*, www.thelancet.com (2005), pp. 1-13.

The Allhat Officers ad Coordinators of the Allhat Collaborative Research Group, *Major Cardiovascular Events in Hypertensive Patients Randomized to Doxazosin vs. Chlorthalidone*, JAMA (2000) vol. 283, No. 15, 1967-75.

CARDURA® (doxazosin mesylate) Tablets, Pfizer Inc. (2002) pp. 1-19.

Thalitone®, Monarch Pharmaceuticals® (2004).

Chemical Abstracts, vol. 122, No. 8, Feb. 20, 1995.

E. Swahn E.A.: "Omega-3 ethyl ester concentrate decreases total apolipoprotein CIII and increases antithrombin III in postmyocardial infarction patients" Clinical Drug Investigation, vol. 15, No. 6, 1998, pp. 473-482.

Hazra et al.,"Pharmacology and Therapeutic Potential of the n-3 Polyunsaturated Fatty Acids, Eicosapentanoic Acid (EPA) and Docosahexaenoic Fatty Acid (DHA) in Fish Oils" Indian Journal of Pharmacology, vol. 31, Aug. 1999, pp. 274-264; XP008002754.

Israel DH, "Fish Oils in the Prevention of Atheroscerosis", J Am Coll Cardiol, Jan. 1992 19(1): 174-85.

Pakala, R et al., "Vascular Smooth Muscle Cells Preloaded with Eicosapentaenoic Acid and Docosahexaenic Acid Fail to Respond to Serotin Stimulation" Atherosclerosis (Shannon, Ireland) (2000), 153(1), 47+57; XP001075031.

Database WPI, Week 199528 Derwent Publications Ltd., London, GB, AN 1995-209347 (1995) XP002197622.

The Merck Manual of Diagnosis and Therapy, 14th ed., published 1982 by Merck & Co., Inc. (NJ), p. 508.

"Protocollo dello studio GISSI-Prevenzione studio di intervento preventive sulle componenti aterosclerotica a trombotica del rischio post-infarto", G. Ital, Cariol, vol. 23, 1053-1061, no date provided.

Cardiologia, 36(7), advertisement page for "Esapent" No date provided.

G, Ital., Cardiol., vol. 21, advertisement page for "Eskim" No date provided.

G, Ital., Cardiol., vol. 21, advertisement page for "Seacor" No date provided.

GISSI-Prevenzione et Al., "Il quadro di riferimento biochimico, farmacologico, epidemilogico del GISSI-prevenzione", G Ital. Cardiol., vol. 23, 933-964(1993).

Roberto Marchioli, et al., *"The Biochemical Pharmacological and Epidemiological Frame of Reference of the GISSI Prevention Study"*, pp. 1-13, GISSI Prevention Study Group, Florence, Mario Negri Institute, Millan (English Translation) Date Unavailable.

\* cited by examiner

ESSENTIAL FATTY ACIDS IN THE PREVENTION OF CARDIOVASCULAR EVENTS

CROSS-REFERENCE TO RELATED APPLICATIONS

This is the U.S. National Stage of PCT/EP00/00957, filed Feb. 7, 2000, which claims priority to Italian patent application no. MI99A000313, filed Feb. 17, 1999, both of which are incorporated herein in their entirety by reference.

This invention concerns the use of a pharmaceutical composition containing essential fatty acid ethyl esters originating from fish oils, in particular as a high concentration mixture of ethyl esters of (20:5ω 3) eicosapentaenoic acid (EPA) and (22:6ω 3) docosahexaenoic acid (DHA) in the prevention of cardiovascular events, especially of mortality in patients who have survived the hospitalization phase of acute myocardial infarction (AMI).

It is well known that certain essential fatty acids contained in fish oil have a therapeutic effect in the prevention and treatment of cardiovascular disorders, such as in the treatment of thrombosis, hypercholesterolemia, arteriosclerosis, cerebral infarction and hyperlipemias.

U.S. patents U.S. Pat. No. 5,502,077, U.S. Pat. No. 5,656,667 and U.S. Pat. No. 5,698,594 can be quoted as examples.

From the above prior art, it is known in particular the utility of fatty acids belonging to the ω-3 family, more specifically (20:5ω 3) eicosapentaenoic acid (EPA) and (22:6ω 3) docosahexaenoic acid (DHA) in treating the above-mentioned disorders.

Indeed EPA, being a precursor of PGI3 and TxA3, exerts a preventing platelet aggregation effect and an antithrombotic effect that can be ascribed to inhibition of cyclooxygenase (similar effect to that of aspirin) and/or to competition with arachidonic acid for this enzyme, with consequent reduction in the synthesis of PGE2 and TxA2. which are well known platelet aggregating agents.

On the other hand DHA is the most important component of cerebral lipids in man and furthermore, being a structural component of the platelet cell, it intervenes indirectly in increasing platelet fluidity, thus playing an important role in antithrombotic activity.

International patent application WO89/11521, whose description is herein incorporated by reference, describes in particular an industrial process for extracting mixtures with a high content in poly-unsaturated acids, including EPA and DHA and their ethyl esters, from animal and/or vegetable oils.

Mixtures of fatty acids, especially EPA/DHA, obtained according to WO89/11521, are reported to be particularly useful in the treatment of cardiovascular diseases.

However, currently used treatments in human therapy have been shown to be insufficient in preventing cardiovascular events, and more specifically mortality, in particular due to sudden death, which happen in patients who have had a myocardial infarction, on account of recurrences after a first acute myocardial infarction episode.

Therefore, there still is the need for an effective drug, in particular for preventing these recurrences.

Object of this invention, therefore, is the use of essential fatty acids with a high content in EPA-ethyl ester or DHA-ethyl ester or a high concentration mixture thereof, in the preparation of a medicament useful for preventing mortality, due, for instance, to cardiovascular events or sudden death, in patients who have suffered from a myocardial infarction. According to a preferred aspect this invention therefore provides the use of essential fatty acids with a high content in EPA-ethyl ester or DHA-ethyl ester or a high concentration mixture thereof, in the preparation of a medicament useful for preventing sudden death in patients who have suffered from a myocardial infarction.

For ease of description "EPA-ethyl ester" and "DHA-ethyl ester" will be also quoted here as "EPA" and "DHA".

An essential fatty acid with high content in EPA-ethyl ester or DHA-ethyl ester, according to the present invention, preferably contains more than 25% by weight (b.w.), in particular from about 60 to about 100% of such ester.

These compounds can be obtained by known methods.

In an essential fatty acid with a high concentration mixture of EPA-ethyl ester and DHA-ethyl ester, preferably such mixture has a content in EPA+DHA greater than 25% by weight, in particular from about 30 to about 100% by weight, preferably about 85% by weight.

In the EPA/DHA mixture, EPA preferably is present in a percentage from about 40 to about 60% by weight and DHA, preferably in a percentage from about 25 to about 45-50%.

In any case, the preferred EPA/DHA ratio in such EPA/DHA mixture is about 0.9-1.5.

Pharmacology

The efficacy of the treatment, according to the invention, is, for instance, proven by the fact that a surprising and highly significant reduction in post-infarction mortality was observed by such treatment in a clinical trial that lasted for 3.5 years, with protocols substantially designed as follows:

1 a "control" group received the standard therapy which is usually given to infarcted patients;

2 a "treatment" group, besides the therapy that was given to the "control" group, received 85% EPA+DHA (1 g daily);

3 a "treatment" group, besides the therapy that was given to the "control" group received vitamin E; and 4 a "treatment" group, besides the therapy that was given to the control group, received vitamin E and 85% EPA+DHA (1 g daily).

In fact the group of patient "treated" according to protocol 2 showed, in comparison to "control" group 1, a decrease of about 20% in total mortality, with a decrease of about 40% of mortality due to sudden death and a notable reduction in mortality due to other cardiovascular events. On the contrary, no significant results were achieved in group 3 as compared to the control group 1, whereas there was a reduction in total mortality of about 19% in group 4 as compared to the control group, with results that were similar to those obtained in treated group 2. From the above clinical results, the person skilled in the art will appreciate that, the use of a pharmaceutical composition in accordance to the present invention is certainly useful in human therapy in preventing mortality in patients who have suffered from a myocardial infarction.

Accordingly, this invention provides a method for preventing mortality in a patient who has survived a myocardial infarction, comprising administering to such patient a therapeutically effective amount of a medicament containing essential fatty acids with a high content in EPA-ethyl ester or DHA-ethyl ester or a high concentration mixture thereof. As known, sudden death is an important contributor to the mortality rate in patients with cardiac disease, accounting for over 450,000 death per year in the USA.

About 80% of such patients, particularly those survivors of acute myocardial infarction with low ventricular ejection fractions, are at high risk of sudden death or reinfarction.

The above clinical results show that the present invention provides a new and valuable therapeutic tool for preventing sudden death in patients in particular in those who survived acute myocardial infarction.

Accordingly, as a preferred aspect, the present invention also provides a method for preventing sudden death in a patient, who is survivor of myocardial infarction, comprising administering to such patient a therapeutically effective amount of a medicament containing essential fatty-acids with a high content in EPA-ethyl ester or DHA-ethyl ester or a high concentration mixture thereof.

The essential fatty acids, according to the invention, can either have a high content, for instance more than 25% b.w., in EPA-ethyl ester or DHA-ethyl ester or in a mixture thereof. However EPA-ethyl ester and DHA-ethyl ester are preferably present as a mixture thereof with a content in EPA+DHA- higher than 25% b.w, in particular from about 30 to about 100% b.w., preferably about 85% b.w.

Based on the obtained clinical results, according to a preferred aspect of the invention, the dosage of an essential fatty acid containing a EPA+DHA mixture with 85% b.w. titer for oral administration to a patient may vary from about 0.7 g to about 1.5 g daily, preferably about 1 g daily.

This amount of product as EPA+DHA mixture (or amount of EPA-ethyl ester alone or DHA-ethyl ester alone) may be administered in several divided doses throughout the day or preferably in a single administration, in order to achieve the desired hematic level. Obviously it is at the 1-5 discretion of the physician to adjust the quantity of product to be administered according to the age, weight and general conditions of the patient.

The medicament, e.g. in the form of a pharmaceutical composition, according to this invention can be prepared according to known methods in the art. The preferred route of administration is the oral one, however leaving alternative routes of administration, such as the parenteral route, to the discretion of the physician.

The following examples illustrate preferred formulations for oral administration, but do not intend to limit the invention in any way.

Gelatin Capsules

According to known pharmaceutical techniques, capsules having the composition below and containing 1 g of active ingredient (EPA+DHA, 85% titer) per capsule are prepared.

| Formulation 1 | |
| --- | --- |
| EPA-ethyl ester | 525 mg/capsule; |
| DHA-ethyl ester | 315 mg/capsule; |
| d-alpha tocopherol | 4 IU/capsule; |
| gelatin | 246 mg/capsule |
| glycerol | 118 mg/capsule; |
| red iron oxide | 2.27 mg/capsule; |
| yellow iron oxide | 1.27 mg/capsule |
| Formulation 2 | |
| Ethyl esters of poly-unsaturated fatty acids with content in ethyl esters of ω-3 poly-unsaturated esters (eicosapentaenoic EPA docosahexaenoic (DHA) | 1000 mg |
| | 850 mg |
| d-l-α tocopherol | 0.3 mg |
| gelatin succinate | 233 mg |
| glycerol | 67 mg |
| sodium p-oxybenzoate | 1.09 mg |
| sodium propyl p-oxobenzoate | 0.54 mg |

The invention claimed is:

1. A method of reducing the incidence of mortality caused by the reoccurrence of cardiovascular events in a patient who has survived a myocardial infarction, comprising administering to said patient a therapeutically effective amount of a medicament containing essential fatty acids containing a mixture of eicosapentaenoic acid ethyl ester (EPA) and docosahexaenoic acid ethyl ester (DHA) wherein the content of EPA+DHA in the mixture is from about 60 to about 100% by weight, and wherein the medicament is administered orally at an essential fatty acids dosage of from about 0.7 g to about 1.5 g daily.

2. The method according to claim 1, wherein the content of EPA+DHA in the mixture is about 85% by weight.

3. The method according to claim 1, wherein the medicament is administered orally at an essential fatty acids dosage of about 1 g daily.

4. The method according to claim 1, wherein the content of EPA in the EPA+DHA mixture is from about 40 to about 60% by weight.

5. The method according to claim 1, wherein the content of DHA in the EPA+DHA mixture is from about 25 to about 50% by weight.

6. The method according to claim 1, wherein the EPA content of the EPA+DHA mixture is from about 40 to about 60% by weight and the DHA content of the EPA+DHA mixture is from about 25 to about 50% by weight.

7. A method of reducing the incidence of sudden death caused by the reoccurrence of cardiovascular events in a patient who has survived a myocardial infarction, comprising administering to said patient a therapeutically effective amount of a medicament containing essential fatty acids containing a mixture of eicosapentaenoic acid ethyl ester (EPA) and docosahexaenoic acid ethyl ester (DHA) wherein the content of EPA+DHA in the mixture is from about 60 to about 100% by weight, and wherein the medicament is administered orally at an essential fatty acids dosage of from about 0.7 g to about 1.5 g daily.

8. The method according to claim 7, wherein the content of EPA+DHA in the mixture is about 85% by weight.

9. The method according to claim 7, wherein the medicament is administered orally at an essential fatty acids dosage of about 1 g daily.

10. The method according to claim 7, wherein the content of EPA in the EPA+DHA mixture is from about 40 to about 60% by weight.

11. The method according to claim 7, wherein the content of DHA in the EPA+DHA mixture is from about 25 to about 50% by weight.

12. The method according to claim 7, wherein the EPA content of the EPA+DHA mixture is from about 40 to about 60% by weight and the DHA content of the EPA+DHA mixture is from about 25 to about 50% by weight.

13. A method of reducing the incidence of mortality caused by the reoccurrence of cardiovascular events in a patient who has survived a myocardial infarction, comprising administering to said patient oral dosage forms comprising 1 g of oil containing ethyl esters of polyunsaturated fatty acids comprising omega-3 fatty acids comprising a mixture of eicosapentaenoic acid (EPA) and docosahexaenoic acid (DHA) wherein the content of EPA+DHA in the oil is from about 60 to about 100% by weight, in an amount effective to reduce the incidence of mortality in the patient.

14. The method according to claim 13, wherein the content of EPA+DHA in the oil is about 85% by weight.

15. The method according to claim 13, wherein the content of EPA in the EPA+DHA mixture is from about 40 to about 60% by weight.

16. The method according to claim 13, wherein the content of DHA in the EPA+DHA mixture is from about 25 to about 50% by weight.

17. The method according to claim 13, wherein the EPA content of the EPA+DHA mixture is from about 40 to about 60% by weight and the DHA content of the EPA+DHA mixture is from about 25 to about 50% by weight.

18. A method of reducing the incidence of sudden death caused by the reoccurrence of cardiovascular events in a patient who has survived a myocardial infarction, comprising administering to said patient oral dosage forms comprising 1 g of oil containing ethyl esters of polyunsaturated fatty acids comprising omega-3 fatty acids comprising a mixture of eicosapentaenoic acid (EPA) and docosahexaenoic acid (DHA) wherein the content of EPA+DHA in the oil is from about 60 to about 100% by weight, in an amount effective to reduce the incidence of sudden death in the patient.

19. The method according to claim 18, wherein the content of EPA+DHA in the oil is about 85% by weight.

20. The method according to claim 18, wherein the content of EPA in the EPA+DHA mixture is from about 40 to about 60% by weight.

21. The method according to claim 18, wherein the content of DHA in the EPA+DHA mixture is from about 25 to about 50% by weight.

22. The method according to claim 18, wherein the EPA content of the EPA+DHA mixture is from about 40 to about 60% by weight and the DHA content of the EPA+DHA mixture is from about 25 to about 50% by weight.

23. The method of claim 1, wherein the content of EPA+DHA in the mixture is about 85% by weight; wherein the medicament is administered orally at an essential fatty acids dosage of about 1g daily; and wherein the EPA content of the EPA+DHA mixture is from about 40 to about 60% by weight and the DHA content of the EPA+DHA mixture is from about 25 to about 50% by weight.

24. The method of claim 7, wherein the content of EPA+DHA in the mixture is about 85% by weight; wherein the medicament is administered orally at an essential fatty acids dosage of about 1 g daily; and wherein the EPA content of the EPA+DHA mixture is from about 40 to about 60% by weight and the DHA content of the EPA+DHA mixture is from about 25 to about 50% by weight.

25. The method of claim 13, wherein the content of EPA+DHA in the mixture is about 85% by weight, and wherein the EPA content of the EPA+DHA mixture is from about 40 to about 60% by weight and the DHA content of the EPA+DHA mixture is from about 25 to about 50% by weight.

26. The method of claim 18, wherein the content of EPA+DHA in the mixture is about 85% by weight, and wherein the EPA content of the EPA+DHA mixture is from about 40 to about 60% by weight and the DHA content of the EPA+DHA mixture is from about 25 to about 50% by weight.

* * * * *